US00PP25700P2

(12) United States Plant Patent
Wood

(10) Patent No.: US PP25,700 P2
(45) Date of Patent: Jul. 14, 2015

(54) ***THUJA* PLANT NAMED 'SMTOBP'**

(50) Latin Name: *Thuja occidentalis*
Varietal Denomination: SMTOBP

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 13/987,823

(22) Filed: Sep. 7, 2013

(51) Int. Cl.
*A01H 7/00* (2006.01)

(52) U.S. Cl.
USPC ..... Plt./213

(58) Field of Classification Search
USPC ..... Plt./213
See application file for complete search history.

(56) References Cited

PUBLICATIONS

Internet publication springmeadownursery.com/plant/84100, Arborvitae named 'Skywalker' (SMTOBP), © 2010.*

* cited by examiner

*Primary Examiner* — Anne Grunberg
(74) *Attorney, Agent, or Firm* — C. A. Whealy

(57) ABSTRACT

A new and distinct cultivar of *Thuja* plant named 'SMTOBP', characterized by its upright plant habit; narrow columnar plant form; vigorous growth habit; dense and bushy form; bright green-colored developing leaves; bright green coloration maintained during the winter; and good winter hardiness and wind resistance.

1 Drawing Sheet

Botanical designation: *Thuja occidentalis.*
Cultivar denomination: 'SMTOBP'.

BACKGROUND OF THE INVENTION

The present invention relates to a new and distinct cultivar of *Thuja* plant, botanically known as *Thuja occidentalis*, commonly known as American Arborvitae and hereinafter referred to by the name 'SMTOBP'.

The new *Thuja* plant is a product of a planned breeding program conducted by the Inventor in Grand Haven, Mich. The objective of the breeding program was to develop new *Thuja* plants with a compact plant habit.

The new *Thuja* plant originated from an open-pollination during the spring of 2003 of the *Thuja occidentalis* 'Brandon', not patented, as the female, or seed parent and an unknown selection of *Thuja occidentalis* as the male, or pollen, parent. The new *Thuja* plant was discovered and selected by the Inventor during the spring of 2006 as a plant within the progeny of the stated open-pollination in a controlled outdoor nursery environment in Grand Haven, Mich.

Asexual reproduction of the new *Thuja* plant by hardwood cuttings in a controlled environment in Grand Haven, Mich. since November, 2007, has shown that the unique features of this new *Thuja* plant are stable and reproduced true to type in successive generations.

SUMMARY OF THE INVENTION

Plants of the new *Thuja* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'SMTOBP'. These characteristics in combination distinguish 'SMTOBP' as a new and distinct *Thuja* plant:

1. Upright plant habit; narrow columnar plant form.
2. Vigorous growth habit.
3. Dense and bushy form.
4. Bright green-colored developing leaves; bright green coloration maintained during the winter.
5. Good winter hardiness and wind resistance.

Plants of the new *Thuja* can be compared to plants of the female parent, 'Brandon'. Plants of the new *Thuja* differ primarily from plants of 'Brandon' in the following characteristics:

1. Plants of the new *Thuja* are narrower than plants of 'Brandon'.
2. Plants of the new *Thuja* grow faster than plants of 'Brandon'.

Plants of the new *Thuja* can be compared to plants of *Thuja occidentalis*, 'DeGroot's Spire', not patented. In side-by-side comparisons conducted in Grand Haven, Mich., plants of the new *Thuja* differed primarily from plants of 'DeGroot's Spire' in the following characteristics:

1. Plants of the new *Thuja* were narrower than plants of 'DeGroot's Spire'.
2. Plants of the new *Thuja* grew faster than plants of 'DeGroot's Spire'.
3. Plants of the new *Thuja* had brighter green-colored leaves than plants of 'DeGroot's Spire'.
4. Plants of the new *Thuja* were more winter hardy than plants of 'DeGroot's Spire'.

BRIEF DESCRIPTION OF THE PHOTOGRAPH

The accompanying colored photograph illustrates the overall appearance of the new *Thuja* plant showing the colors as true as it is reasonably possible to obtain in colored reproductions of this type. Colors in the photograph may differ slightly from the color values cited in the detailed botanical description which accurately describe the colors of the new *Thuja* plant.

The photograph comprises a side perspective view of a typical plant of 'SMTOBP'.

DETAILED BOTANICAL DESCRIPTION

The aforementioned photograph and following observations, measurements and values describe plants grown during the spring and summer in ground beds in an outdoor nursery in Grand Haven, Mich. and under cultural practices typical of commercial *Thuja* plant production. The plant in the photograph is seven years old and the plants used for the description were two years old. In the following detailed description, color references are made to The Royal Horticultural Society Colour Chart, 2001 Edition, except where general terms of ordinary dictionary significance are used.

Botanical classification: *Thuja occidentalis* 'SMTOBP'.

Parentage:

*Female, or seed, parent.*—*Thuja occidentalis* 'Brandon', not patented.

*Male, or pollen, parent.*—Unknown selection of *Thuja occidentalis*, not patented.

Propagation:

*Type.*—By hardwood cuttings.

*Time to initiate roots, summer.*—About 45 days at temperatures about 10° C. to 27° C.

*Time to produce rooted young plants, summer.*—About six months at temperatures about 10° C. to 27° C.

*Root description.*—Thick to fine.

*Rooting habit.*—Freely branching; dense.

Plant description:

*Plant and growth habit.*—Perennial evergreen shrub; upright plant habit and narrowly columnar plant form; vigorous growth habit; moderate growth rate.

*Plant height.*—About 73 cm.

*Plant diameter, base.*—About 23 cm.

*Branching habit.*—Freely branching habit with about seven primary lateral branches developing per plant with numerous secondary and tertiary branches; dense and bushy habit.

*Lateral branch description.*—Length: About 25 cm. Diameter: About 4 mm. Internode length: About 3.5 cm. Aspect: Main branch, upright; lateral branches about 20° to 40° from stem axis. Strength: Strong. Texture, developing branches: Scaly; glabrous. Texture, main trunk: Woody. Color, developing branches: Close to 194A. Color, developed branches: Close to 165A.

*Leaf description.*—Appearance and arrangement: Flattened and closely appressed, scale-like; opposite, simple; sessile. Length: About 3 mm. Width: About 2 mm. Shape: Ovate. Apex: Acute. Base: Obtuse. Margin: Entire. Venation pattern: Parallel. Texture: Smooth, glabrous. Color: Developing leaves, upper and lower surfaces: Close to 144A; color is maintained during the winter. Fully expanded leaves, upper and lower surfaces: Close to 137A; venation, close to 137A.

Cone description: Cone development has not been observed on plants of the new *Thuja*.

Garden performance: Plants of the new *Thuja* have been observed have good garden performance, good winter hardiness, to be wind-tolerant and to tolerate temperatures ranging from about −31° C. to about 38° C.

Pathogen & pest resistance: Plants of the new *Thuja* have been observed to be resistant to root rot pathogens. Plants of the new *Thuja* have not been observed to be resistant to pests and other pathogens common to *Thuja* plants.

It is claimed:

1. A new and distinct *Thuja* plant named 'SMTOBP' as illustrated and described.

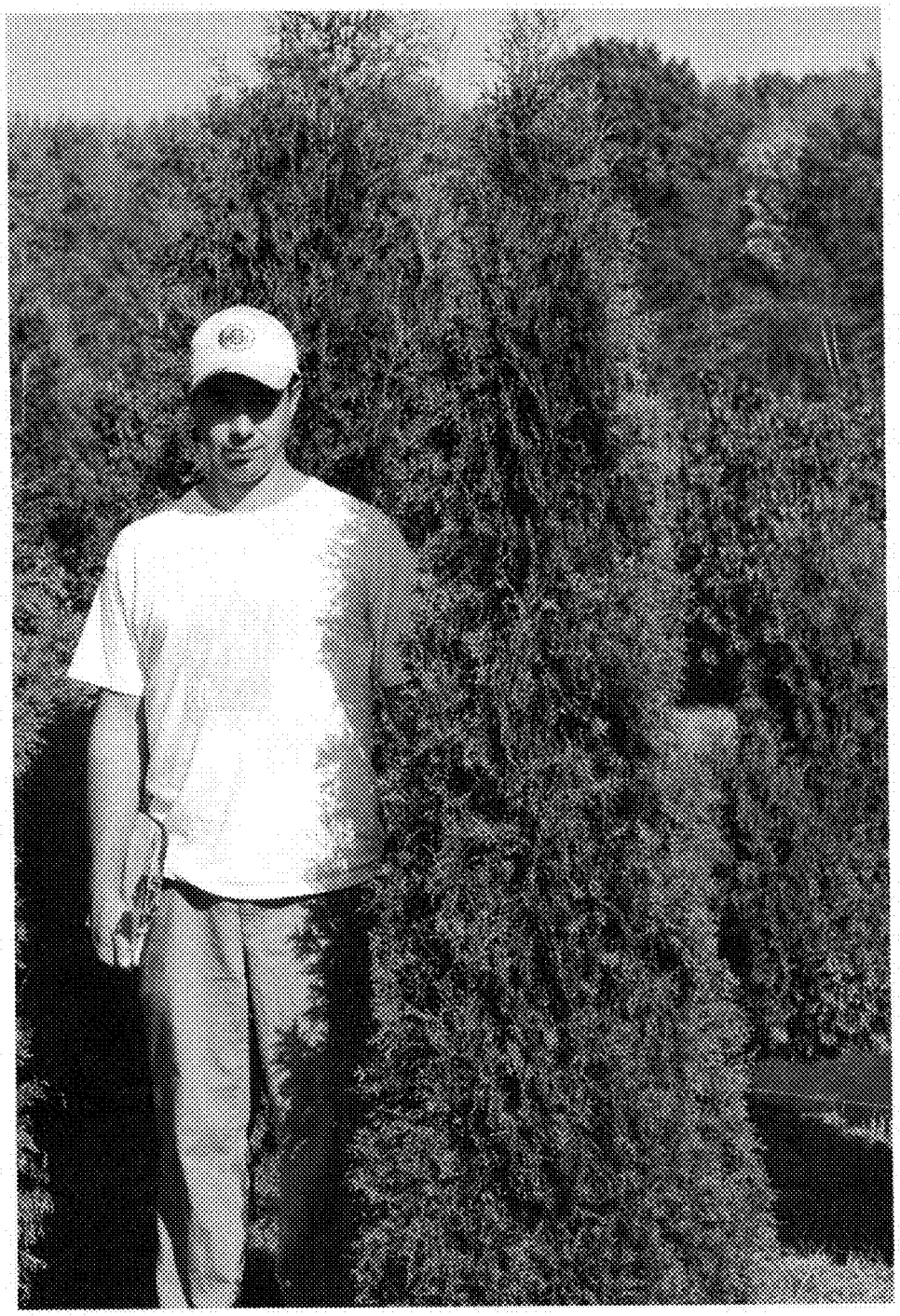

* * * * *